US00PP17881P2

(12) United States Plant Patent
Gerawan

(10) Patent No.: US PP17,881 P2
(45) Date of Patent: Jul. 24, 2007

(54) PLUM TREE NAMED 'BLACK DELIGHT'

(50) Latin Name: *Prunus Salicina*
Varietal Denomination: Black Delight

(75) Inventor: Mike Gerawan, Reedley, CA (US)

(73) Assignee: Gerawan Farming, Sanger, CA (US)

( * ) Notice: Subject to any disclaimer, the term of this patent is extended or adjusted under 35 U.S.C. 154(b) by 0 days.

(21) Appl. No.: 11/359,930

(22) Filed: Feb. 21, 2006

(51) Int. Cl.
*A01H 5/00* (2006.01)

(52) U.S. Cl. ..... Plt./184

(58) Field of Classification Search ..... Plt./184
See application file for complete search history.

*Primary Examiner*—Anne Marie Grunberg
*Assistant Examiner*—S. B. McCormick-Ewoldt
(74) *Attorney, Agent, or Firm*—Townsend and Townsend and Crew LLP

(57) ABSTRACT

A new and distinct variety of plum characterized by producing a freestone fruit with good dark-red coloration that is ripe for commercial harvesting and shipping June 13–15 in the San Joaquin Valley of Central California. The new variety, a plum seedling, is similar to 'Black Beaut' plum tree (unpatented). Fruit from 'Black Delight' is distinguishable and has very good dark coloration, has very good flavor, stores very well, and ripens several days before 'Black Beaut'.

1 Drawing Sheet

Latin name of the genus and species: The plum cultivar of this invention is botanically identified as *Prunus Salicina.*

Variety denomination: The variety denomination is 'Black Delight'.

BACKGROUND OF THE INVENTION

The present invention refers to a new variety of plum tree, which will hereinafter be denominated as 'Black Delight' plum tree. The new variety produces a yellow fleshed plum with a dark red skin, freestone type that is mature for harvesting and shipping during early to mid June in a normal year in the San Joaquin Valley of Central California. The fruit is mid-size with dark red blush.

In the development of new commercial varieties, specific characteristics provide a premium for fruit varieties that mature early or late in the growing season. However, in particular, early varieties lack size, flavor, and coloration or blush. Thereafter, in order for a fruit to be a commercial success, it must be of good size, good flavor, good color, and possess good shipping and storage characteristics. In addition, maturity date should be different from other similar fruit. This new invention meets the aforementioned characteristics and therefore should be of commercial appeal to the consumer.

BRIEF SUMMARY OF THE INVENTION

The 'Black Delight' plum tree is characterized by producing a medium size freestone fruit which has very good dark-red blush coloration and is ripe for commercial harvesting or shipping around June 10–15 in a normal year in the San Joaquin Valley of Central California as a mid-sized fruit with dark red blush and yellow flesh. The new variety is most similar to 'Black Beaut' (unpatented) from which it is distinguished in that it ripens several days before the 'Black Beaut' variety. The fruit of this variety is medium size with good colors making it greatly acceptable to the consumer. No information is available on the new variety's susceptibility or resistance to disease. Several different plum varieties have been used as pollinators: 'Catalina' (not patented), '5-100' (U.S. Plant Pat. No. 8,057) and 'Ambra' (not patented).

DETAILED DESCRIPTION OF THE INVENTION

Figure 1:
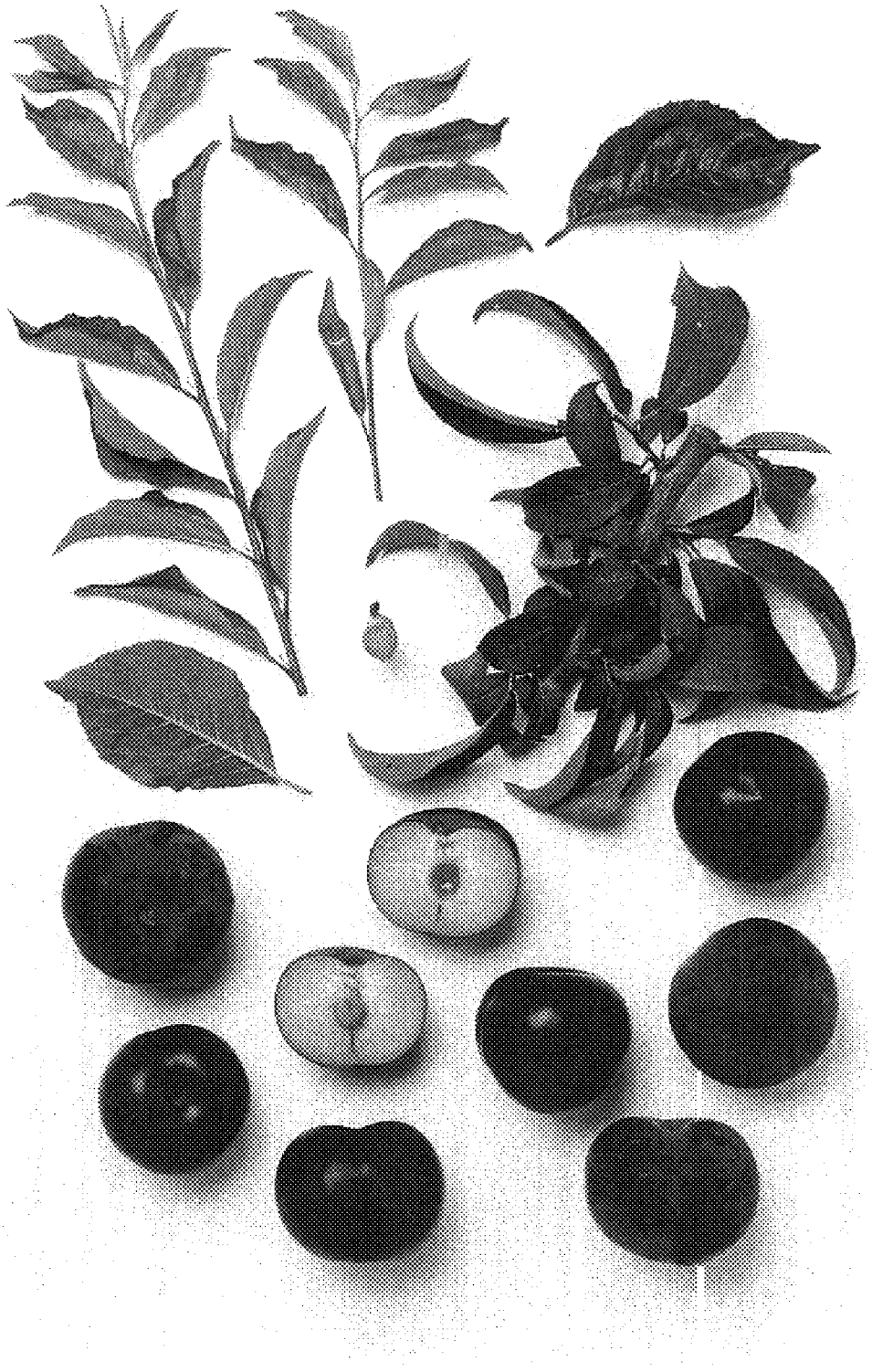
FIG. 1 illustrates the various views of the fruit displaying the characteristic skin color, shape, and color of the flesh, including, the bottom or stem end of the fruit, the apex of the fruit, the suture side of the fruit, the pit cavity, the pit in the pit cavity, the pit, and the foliage of the new variety of plum tree.

The present invention (variety) was discovered in the inventor's nursery planting as a seedling of unknown parentage in May 2001, which is located on Riverbend Avenue near Sanger, Calif. in the San Joaquin Valley of Central California. The new variety was asexually reproduced by bud grafting on PLUOT® interspecific plum rootstock, enough trees to plant 60 acres at a site north and east of Reedley, Calif. The inventor carefully compared the asexually reproduced trees with the parent seedling including the fruit and they are identical in all respects.

Referring more specifically to the horticultural details of the new and distinct variety of plum tree, the following descriptions have been observed under the ecological condition prevailing at the plum planting from which this fruit and foliage was collected, near Reedley, Calif. in the San Joaquin Valley of Central California. All major color designations are by reference to *A Dictionary of Color* by Maerz and Paul, First Edition, published in 1930. Common colors are also employed.

Tree:

*Age of observed plant.*—4 years old.

*Size.*—Medium for 3rd leaf tree, 8–10 feet high, 6–8 feet wide.

*Vigor.*—Very good.
*Shape.*—Upright and spreading.
*Productivity.*—Very good for 3rd leaf tree with regular bearing.
*Chilling requirements.*—Normal for plum trees in the Central San Joaquin Valley of California.

Trunk:
*Size.*—Medium-large, 23–27 inches in circumference, 12 inches above ground.
*Surface texture.*—Rough.
*Color code.*—P1.56 A2 — Kara Dagh.
*Lenticels.*—5 per square inch (20 lenticels were counted over a 4 inch length of trunk). Lenticel Size — 1–2 mm (0.04–0.079 inch) in length. Lenticel Color — P1.56 H2 — Lt Brown.

Branches:
*Size.*—Medium to large — 12 to 16 inches in circumference. 14 inches above crotch — angle of branches approximately 62°.
*Color of branches over 1 year.*—P1.55 A3 Pigeon.
*Color of branches less than 1 year.*—P1.21 L6 — Parrot gr.
*Texture of mature branches.*—Slightly rough.

Leaves:
*Size.*—Medium, pinnately veined. Length — 84–101 mm (3.31–3.98 inches). Width — 45–53 mm (1.71–2.09 inches).
*Shape.*—Ovate.
*Base shape.*—Rounded.
*Apex shape.*—Acuminate.
*Texture.*—Smooth.
*Margin.*—Double serration.
*Glands.*—21-3 reniform — small — 2 mm (0.08 inch) — Color — P1.20 K6 Piquant gr.
*Stiples.*—One — reddish brown — 4 mm (0.16 inch).
*Color.*—Upper surface — P1.24 J12 near Chrome gr., deep. Lower surface — P1.22 K7 Spinach gr.
*Petiole.*—11–14 mm (0.43–0.55 inch), diameter — 2 mm (0.08 inch). Color — P1.21 L6 Parrot gr.
*Midvein.*—Approximately 2 mm (0.08 inch). Color — P1.21 L6 Parrot gr.
*Venation pattern.*—Pinnately.

Flowers:
*Flower buds.*—Clusters of 2 to 3. Shape — conic. Size — length — 7.9 mm (0.31 inch). Width — 5–6 mm (0.20–0.24 inch).
*Calyx.*—5 sepals — color — P1. 19 K6 Sea green.
*Flowers.*—Clusters 2 to 3. Date of Bloom — 75% February 23.
*Diameter when fully opened.*—22–26 mm (0.87–1.02 inch).
*Petals.*—5. Size — small. Length — 10–11 mm (0.39–0.43 inch). Width — 8–9 mm (0.31–0.35 inch). Form — broadly ovate. Color — white. Claw — small — 1 mm (0.04 inch). Petal Margins — undulate. Pedicel — 8–10 mm (0.31–0.39 inch). Color — P1. 17 I6 — Viridine gr.
*Sepals.*—5. Color — green — P1.19 K6 Sea gr. Length — 4–6 mm (0.16–0.21 inch). Width — 5 mm (0.20 inch).
*Stamens.*—25–28.
*Filament white.*—5–8 mm long (0.20–0.31 inch).
*Anthers.*—Small — P1. 13 L11 Peruvian br.
*Pistil.*—1 — 7–8 mm (0.28–0.31 inch).
*Fertility.*—3 pollinizers used 'Catalina' plum (not patented) 28% '5-100' Plum (U.S. Plant Pat. No. 8,057), 17% 'Ambra' plum (not patented).

Fruit:
*Date of maturity.*—June 10–15.
*Size.*—Medium. Diameter of Axial Plane — 47–56 mm (1.85–2.20 inch). Transverse in Suture plane — 58–62 mm (2.28–2.44 inch). Transverse at Right Angles to Suture Plane — 52–59 mm (2.05–2.32 inch).
*Form.*—Nearly uniform, symmetrical — ventral surface smooth.
*Stem cavity.*—Length — 15–17 mm (0.59–0.67 inch). Width — 12–14 mm (0.47–0.55 inch). Depth — 7–10 mm (0.28–0.39 inch).
*Stem.*—Length — 12 mm (0.47 inch). Width — 2 mm (0.08 inch). Apex — Round. Pistil point — Not noticeable.
*Skin.*—Thickness normal for plum. Texture — firm. Color Blush color — P1.55 L8 Rubient to P1.56 H9 Old Burgundy. Ground Color — P1. 7 L6 India Red, Arabian Red and Red Robbin.
*Flesh.*—P1.12 C3 Old Ivory.
*Color of surface of pit cavity.*—P1.12 L3 Pyrite Y.
*Color of pit well.*—P1.13 L5 Bistre gr.
*Pit well.*—Length — 14 mm (0.55 inch). Width — 15 mm (0.59 inch). Depth — 8 mm (0.32 inch).
*Shipping and storage characteristics.*—The fruit can be stored for 30 days at 32 degrees Fahrenheit.

Stone:
*Freestone.*—Fibers few.
*Size.*—Length — 16–18 mm (0.63–0.71 inch). Width — 14–16 mm (0.55–0.63 inch). Thickness — 10 mm (0.39 inch).
*Form.*—Ovate.
*Apex shape.*—Somewhat rounded with small point.
*Base.*—Flattened.
*Color code.*—P1.5 H10 Rosewood.
*Sides.*—Ventral wing; dorsal side ridged from apex to base.
*Surface.*—Grooved with grooves most prominent at basal end.
*Tendency to split.*—None observed.
*Use.*—Fresh market.
*Keeping quality.*—Very good.

The above description of this new variety of plum tree is based on the growing conditions prevalent in the Reedley area of the San Joaquin Valley of Central California: variations of the usual magnitude, such as differences in maturity date, may be due to cultural practices including irrigation, fertilization, pruning, fruit thinning and primary climate changes.

What is claimed is:

1. A new and distinct variety of plum tree having characteristics described and illustrated herein.

* * * * *